US011440875B2

(12) United States Patent
Higashi et al.

(10) Patent No.: US 11,440,875 B2
(45) Date of Patent: Sep. 13, 2022

(54) SULFONIC ACID, CARBOXYLIC ACID, AND SALTS THEREOF

(71) Applicant: DAIKIN INDUSTRIES, LTD., Osaka (JP)

(72) Inventors: Masahiro Higashi, Osaka (JP); Satoru Yoneda, Osaka (JP); Akiyoshi Yamauchi, Osaka (JP); Sumi Ishihara, Osaka (JP); Yosuke Kishikawa, Osaka (JP); Marina Nakano, Osaka (JP); Shinnosuke Nitta, Osaka (JP); Hirokazu Aoyama, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/495,641

(22) PCT Filed: Mar. 30, 2018

(86) PCT No.: PCT/JP2018/013635
§ 371 (c)(1),
(2) Date: Sep. 19, 2019

(87) PCT Pub. No.: WO2018/181907
PCT Pub. Date: Oct. 4, 2018

(65) Prior Publication Data
US 2020/0024229 A1 Jan. 23, 2020

(30) Foreign Application Priority Data

Mar. 31, 2017 (JP) .............................. JP2017-073086

(51) Int. Cl.
*C07C 309/10* (2006.01)
*C07C 53/126* (2006.01)
*C07C 59/347* (2006.01)

(52) U.S. Cl.
CPC .......... *C07C 309/10* (2013.01); *C07C 53/126* (2013.01); *C07C 59/347* (2013.01)

(58) Field of Classification Search
CPC ................ C08F 210/02; C08F 220/286; C08F 290/062; C07C 309/10; C07C 309/07; C07C 53/126; C07C 59/347; C07C 235/74; C07C 59/185; C08K 5/005; C08K 5/14; C08L 2203/202; C08L 2205/02; C08L 2207/066; C08L 23/06; C08L 71/02; H01B 3/441; H01B 3/447; H01B 7/2813; H01B 13/24; C11D 1/04; C11D 1/12; F25B 2313/002; F25B 2313/02741; F25B 30/06; F25B 41/20; F25B 41/40; F25B 6/04
See application file for complete search history.

(56) References Cited

U.S. PATENT DOCUMENTS

| | | | |
|---|---|---|---|
| 3,793,210 A | 2/1974 | Corey | |
| 3,809,649 A * | 5/1974 | Van Doorne et al. | ... C10M 5/00 508/413 |
| 4,075,113 A * | 2/1978 | Van Doorne | ........ C10M 169/00 508/534 |
| 5,010,178 A | 4/1991 | Lal | |
| 5,010,179 A | 4/1991 | Lal | |
| 5,037,963 A | 8/1991 | Lal | |
| 5,043,340 A | 8/1991 | Cullinan | |
| 5,747,537 A * | 5/1998 | Gordon | .................. A61K 31/20 514/558 |
| 6,090,250 A | 7/2000 | Mazzeo et al. | |
| 2012/0121679 A1* | 5/2012 | Cannon | .................. A61P 31/04 424/404 |
| 2016/0037034 A1 | 2/2016 | Inasaki et al. | |
| 2016/0155969 A1 | 6/2016 | Matsumoto et al. | |

FOREIGN PATENT DOCUMENTS

| | | |
|---|---|---|
| CN | 105247391 A | 1/2016 |
| CN | 105393361 A | 3/2016 |
| DE | 27 40 854 A1 | 3/1979 |
| GB | 1081234 A | 8/1967 |
| JP | 49-029294 A | 3/1974 |
| JP | 3-291262 A | 12/1991 |
| JP | 1996-08048625 * | 2/1996 |
| JP | 9-503295 A | 3/1997 |
| JP | 11-29788 A | 2/1999 |
| JP | 2003-005329 A | 1/2003 |
| WO | 95/08529 A1 | 3/1995 |
| WO | 2011/009031 A2 | 1/2011 |
| WO | 2012/116238 A1 | 8/2012 |
| WO | 2013/045662 A1 | 4/2013 |

(Continued)

OTHER PUBLICATIONS

Naodhima et al. (Synthesis of Both Enantiomers of Phoracantholide I, A Defensive Secretion of the Eucarypt Longicorn (*Phoracantha synonyma*), Employing Microbial Asymmetric Reduction with Immobilized Baker's Yeast, Bull. Chem. Soc. Jpm. vol. 62, No. 2 pp. 608-610, Published 1989) (Year: 1989).*
JP1996-08048625 translated (Year: 1996).*
de Mayo et al. (Biphasic photochemistry: Water interaction in functionalized micelles, Tetrahedron Letters vol. 22, Issue 6, pp. 509-512, Published 1981) (Year: 1981).*
Gould (Salt Selection for Basic Drugs, International Journal of Pharmaceutics, 33, pp. 201-217, Published 1986) (Year: 1986).*
International Preliminary Report on Patentability with translation of Written Opinion dated Oct. 1, 2019, in International Application No. PCT/JP2018/013635.

(Continued)

*Primary Examiner* — Yevgeny Valenrod
*Assistant Examiner* — Blaine G Doletski
(74) *Attorney, Agent, or Firm* — Sughrue Mion, PLLC

(57) ABSTRACT

A sulfonic acid or carboxylic acid containing a carbonyl group, or a salt thereof represented by the following formula:

$$R^1-C(=O)-(CR^2{}_2)_n-(OR^3)_p-(CR^4{}_2)_q-L-A$$

wherein $R^1$, $R^2$, $R^3$, $R^4$, n, p, q, A and L are as defined herein.

10 Claims, No Drawings

(56) References Cited

FOREIGN PATENT DOCUMENTS

| WO | WO2013/045662 | * | 4/2013 |
| WO | 2015/012107 A1 | | 1/2015 |

OTHER PUBLICATIONS

A. Muga et al., "Water Penetration and Phase Behavior of Surfactant Gel Phases and Lipid Bilayers", The Journal of Physical Chemistry, 1990, pp. 7265-7271, vol. 94, No. 18.

International Search Report for PCT/JP2018/013635 dated Jun. 5, 2018 [PCT/ISA/210].

Chen, D. et al., "Effect of detergent chaps on micro-surroundings in purple membrane bilayer", ACTA English Biophysica Sinica, Dec. 2000, vol. 16, No. 4, pp. 801-805 (total 6 pages).

M. Kitamura et al., "Asymmetric synthesis of beta-hydroxy sulfonic acids by BINAP/Ru-catalyzed hydrogenation", Tetrahedron, vol. 55, No. 29, Jul. 16, 1999, pp. 8769-8785 (17 pages).

S. Hiranuma et al., "Synthesis of homoharringtonine and its derivative by partial esterification of cephalotaxine", Tetrahedron Letters, vol. 23, No. 34, Aug. 1982, pp. 3431-3434 (4 pages).

M. Krasavin et al., "New nitrofurans amenable by isocyanide multicomponent chemistry are active against multidrug-resistant and polyresistant *Mycobacterium tuberculosis*", Bioorganic & Medicinal Chemistry, vol. 25, No. 6, Feb. 4, 2017, pp. 1867-1874 (8 pages).

K. Ishihara et al., "Highly diastereoselective acetal cleavages using novel reagents prepared from organoaluminium and pentafluorophenol", Journal of the American Chemical Society, vol. 115, Nov. 1, 1993, pp. 10695-10704 (10 pages).

S.M. Osman, et al.: "Markonikov hydration and amination of 10-undecenoic acid and BF3-catalysed dimethyl sulfoxide oxidation of its methyl epoxide", Fette, Seifen, Anstrichmittel, vol. 77, No. 3, Mar. 1975, pp. 106-108 (3 pages).

Extended European Search Report dated Jan. 22, 2021 from the European Patent Office in Application No. 18778012.

* cited by examiner

SULFONIC ACID, CARBOXYLIC ACID, AND SALTS THEREOF

CROSS REFERENCE TO RELATED APPLICATIONS

This application is a National Stage of International Application No. PCT/JP2018/013635 filed Mar. 30, 2018, claiming priority based on Japanese Patent Application No. 2017-073086 filed Mar. 31, 2017.

TECHNICAL FIELD

The invention relates to sulfonic acids, carboxylic acids, and salts thereof.

BACKGROUND ART

Patent Literature 1 discloses a compound represented by the following formula.

[Chem. 1]

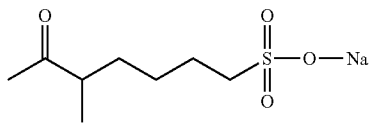

CITATION LIST

Patent Literature

Patent Literature 1: WO 2013/045662

SUMMARY OF INVENTION

Technical Problem

The invention aims to provide a novel sulfonic acid or carboxylic acid containing a carbonyl group, or a salt thereof.

Solution to Problem

The invention relates to a compound represented by the following formula:

[Chem. 2]

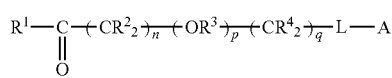

wherein
$R^1$ is a linear or branched alkyl group containing one or more carbon atoms and optionally containing a substituent or a cyclic alkyl group containing three or more carbon atoms and optionally containing a substituent, and optionally contains a monovalent or divalent heterocycle or optionally forms a ring when containing three or more carbon atoms;
$R^2$ and $R^4$ are each individually H or a substituent;
$R^3$ is a C1-C10 alkylene group optionally containing a substituent;
n is an integer of 1 or greater;
p and q are each individually an integer of 0 or greater;

A is $-SO_3X$ or $-COOX$, wherein X is H, a metal atom, $NR^5_4$, imidazolium optionally containing a substituent, pyridinium optionally containing a substituent, or phosphonium optionally containing a substituent, where $R^5$s are each H or an organic group and are the same as or different from each other; and
L is a single bond, $-CO_2-B-*$, $-OCO-B-*$, $-CONR^6-B-*$, $-NR^6CO-B-*$, or $-CO-$ other than the carbonyl groups in $-CO_2-B-$, $-OCO-B-$, $-CONR^6-B-$, and $-NR^6CO-B-$, where B is a single bond or a C1-C10 alkylene group optionally containing a substituent, $R^6$ is H or a C1-C4 alkyl group optionally containing a substituent, and * indicates the bond to A in the formula.

The compound preferably contains 3 to 30 carbon atoms in total.

L is preferably a single bond.

$R^2$ and $R^4$ are preferably each H or a C1-C4 linear or branched alkyl group.

$R^3$ is preferably a C1-C4 alkylene group free from a substituent.

$R^1$ is preferably a C1-C4 linear or branched alkyl group.

In the formula, a sum of n, p, and g is preferably an integer of 6 or greater.

$R^1$ in the formula is preferably a methyl group.

X in the formula is preferably a metal atom or $NR^5_4$, wherein $R^5$ is defined as described above.

The compound is preferably an aqueous dispersant.

Advantageous Effects of Invention

The compound of the invention is a compound exhibiting a surfactant activity, and can suitably be used as an aqueous dispersant.

DESCRIPTION OF EMBODIMENTS

The invention is described in detail below.

The term "organic group" as used herein means a group containing one or more carbon atoms or a group obtainable by removing one hydrogen atom from an organic compound, unless otherwise mentioned.

Examples of the "organic group" include:
an alkyl group optionally containing one or more substituents,
an alkenyl group optionally containing one or more substituents,
an alkynyl group optionally containing one or more substituents,
a cycloalkyl group optionally containing one or more substituents,
a cycloalkenyl group optionally containing one or more substituents,
a cycloalkadienyl group optionally containing one or more substituents,
an aryl group optionally containing one or more substituents,
an aralkyl group optionally containing one or more substituents,
a non-aromatic heterocyclic group optionally containing one or more substituents,
a heteroaryl group optionally containing one or more substituents,
a cyano group,
a formyl group,
RaO—,
RaCO—, RaSO$_2$—,
RaCOO—,
RaNRaCO—,
RaCONRa—,
RaOCO—, and
RaOSO$_2$—,
wherein each Ra is independently
an alkyl group optionally containing one or more substituents,
an alkenyl group optionally containing one or more substituents,
an alkynyl group optionally containing one or more substituents,
a cycloalkyl group optionally containing one or more substituents,
a cycloalkenyl group optionally containing one or more substituents,
a cycloalkadienyl group optionally containing one or more substituents,
an aryl group optionally containing one or more substituents,
an aralkyl group optionally containing one or more substituents,
a non-aromatic heterocyclic group optionally containing one or more substituents, or
a heteroaryl group optionally containing one or more substituents.

The organic group is preferably an alkyl group optionally containing one or more substituents.

The term "substituent" as used herein means a group which can replace another atom or group, unless otherwise mentioned. Examples of the "substituent" include an aliphatic group, an aromatic group, a heterocyclic group, an acyl group, an acyloxy group, an acylamino group, an aliphatic oxy group, an aromatic oxy group, a heterocyclic oxy group, an aliphatic oxycarbonyl group, an aromatic oxycarbonyl group, a heterocyclic oxycarbonyl group, a carbamoyl group, an aliphatic sulfonyl group, an aromatic sulfonyl group, a heterocyclic sulfonyl group, an aliphatic sulfonyloxy group, an aromatic sulfonyloxy group, a heterocyclic sulfonyloxy group, a sulfamoyl group, an aliphatic sulfonamide group, an aromatic sulfonamide group, a heterocyclic sulfonamide group, an amino group, an aliphatic amino group, an aromatic amino group, a heterocyclic amino group, an aliphatic oxycarbonylamino group, an aromatic oxycarbonylamino group, a heterocyclic oxycarbonylamino group, an aliphatic sulfinyl group, an aromatic sulfinyl group, an aliphatic thio group, an aromatic thio group, a hydroxy group, a cyano group, a sulfo group, a carboxy group, an aliphatic oxyamino group, an aromatic oxyamino group, a carbamoylamino group, a sulfamoyl amino group, a halogen atom, a sulfamoyl carbamoyl group, a carbamoyl sulfamoyl group, a dialiphatic oxyphosphinyl group, and a diaromatic oxyphosphinyl group.

The invention relates to a compound represented by the following formula.

[Chem. 3]

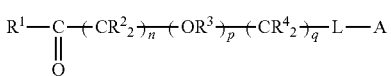

In the formula, R$^1$ is a linear or branched alkyl group containing one or more carbon atoms and optionally containing a substituent or a cyclic alkyl group containing three or more carbon atoms and optionally containing a substituent. R$^1$ is preferably a C1-C4 linear or molecular chain alkyl group.

When containing three or more carbon atoms, the alkyl group may optionally contain a monovalent or divalent heterocycle, or may optionally form a cycle. The heterocycle is preferably an unsaturated heterocycle, more preferably an oxygen-containing unsaturated heterocycle, and may be a furan ring, for example. In R$^1$, a divalent heterocycle may be present between two carbon atoms, or a divalent heterocycle may be present at an end and bind to —C(=O)—, or a monovalent heterocycle may be present at an end of the alkyl group.

The "number of carbon atoms" in the alkyl group herein includes the number of carbon atoms constituting the heterocycles.

The compound preferably contains 3 to 30, more preferably 5 to 25, still more preferably 7 to 20 carbon atoms in total.

The substituent which may be contained in the alkyl group for R$^1$ is preferably a halogen atom, a C1-C10 linear or branched alkyl group, a C3-C10 cyclic alkyl group, or a hydroxy group, particularly preferably a methyl group or an ethyl group.

The alkyl group for R$^1$ is preferably free from a carbonyl group.

In the alkyl group, 75% or less of the hydrogen atoms binding to any of the carbon atoms may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group preferably contains no substituent,

R$^1$ is preferably a C1-C10 linear or branched alkyl group optionally containing a substituent or a C3-C10 cyclic alkyl group optionally containing a substituent, more preferably a C1-C10 linear or branched alkyl group free from a carbonyl group or a C3-C10 cyclic alkyl group free from a carbonyl group, still more preferably a C1-C10 linear or branched alkyl group free from a substituent, further more preferably a C1-C3 linear or branched alkyl group free from a substituent, particularly preferably a methyl group (—CH$_3$) or an ethyl group (—C$_2$H$_5$), most preferably a methyl group (—CH$_3$).

In the formula, R$^2$ and R$^4$ are each individually H or a substituent; multiple R$^2$s may be the same as or different from each other and multiple R$^4$s may be the same as or different from each other.

The substituent, for each of R$^2$ and R$^4$ is preferably a halogen atom, a C1-C10 linear or branched alkyl group, a C3-C10 cyclic alkyl group, or a hydroxy group, particularly preferably a methyl group or an ethyl group.

The alkyl group for each of R$^2$ and R$^4$ is preferably free from a carbonyl group.

In the alkyl group, 75% or less of the hydrogen atoms binding to any of the carbon atoms may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group preferably contains no substituent.

The alkyl group for each of R$^2$ and R$^4$ is preferably a C1-C10 linear or branched alkyl group free from a carbonyl group or a C3-C10 cyclic alkyl group free from a carbonyl group, more preferably a C1-C10 linear or branched alkyl group free from a carbonyl group, still more preferably a C1-C3 linear or branched alkyl group free from a substituent, particularly preferably a methyl group ($—CH_3$) or an ethyl group ($—C_2H_5$).

$R^2$ and $R^4$ are preferably each individually H or a C1-C10 linear or branched alkyl group free from a carbonyl group, more preferably H or a C1-C4 linear or molecular chain alkyl group, still more preferably H or a C1-C3 linear or branched alkyl group free from a substituent, particularly preferably H, a methyl group ($—CH_3$), or an ethyl group ($—C_2H_5$), most preferably H.

$R^3$ is preferably a C1-C4 alkylene group free from a substituent. In the formula, $R^3$ is a C1-C10 alkylene group optionally containing a substituent. When multiple $R^3$s are present, they may be the same as or different from each other.

The alkylene group is preferably free from a carbonyl group.

In the alkylene group, 75% or less of the hydrogen atoms binding to any of the carbon atoms may be replaced by halogen atoms, 50% or less thereof may be replaced by halogen atoms, or 25% or less thereof may be replaced by halogen atoms. The amylene group is preferably a non-halogenated alkyl group containing no halogen atoms such as fluorine atoms and chlorine atoms.

The alkylene group preferably contains no substituent.

The alkylene group is preferably a C1-C10 linear or branched alkylene group optionally containing a substituent or a C3-C10 cyclic alkylene group optionally containing a substituent, preferably a C1-C10 linear or branched alkylene group free from a carbonyl group or a C3-C10 cyclic alkylene group free from a carbonyl group, more preferably a C1-C10 linear or branched alkylene group free from a substituent, still more preferably a methylene group ($—CH_2—$), an ethylene group ($—C_2H_4—$), an isopropylene group ($—CH(CH_3)(CH_2)—$), or a propylene group ($—C_3H_6—$).

Any two of $R^1$, $R^2$, $R^3$, and $R^4$ may bind to each other to form a ring.

In the formula, n is an integer of 1 or greater; n is preferably an integer of 1 to 40, more preferably an integer of 1 to 30, still more preferably an integer of 5 to 25.

In the formula, p and q are each individually an integer of 0 or greater; p is preferably an integer of 0 to 10, more preferably 0 or 1, while q is preferably an integer of 0 to 10, more preferably an integer of 0 to 5.

The sum of n, p, and q is preferably an integer of 6 or greater. The sum of n, p, and q is more preferably an integer of 8 or greater. The sum of n, p, and q is also preferably an integer of 60 or smaller, more preferably an integer of 50 or smaller, still more preferably an integer of 40 or smaller.

In the formula, A is $—SO_3X$ or $—COOX$, wherein X is H, a metal atom, $NR^5_4$, imidazolium optionally containing a substituent, pyridinium optionally containing a substituent, or phosphonium optionally containing a substituent, wherein $R^5$s are each H or an organic group, and are the same as or different from each other. $R^5$ is preferably H or a C1-C10 organic group, more preferably H or a C1-C4 organic group. Examples of the metal atom include alkali metals (Group 1) and alkaline earth metals (Group 2), and preferred is Na, K, or Li.

X is preferably H, a metal atom, or $NR^5_4$, more preferably H, an alkali metal (Group 1), an alkaline earth metal (Group 2), or $NR^5_4$, still more preferably H, Na, K, Li, or $NH_4$, further more preferably Na, K, or $NH_4$, particularly preferably Na or $NH_4$, most preferably $NH_4$.

In the formula, L is a single bond, $—CO_2—B—*$, $—OCO—B—*$, $—CONR^6—B—*$, $—NR^6CO—B—*$, or $—CO—$ other than the carbonyl groups in $—CO_2—B—$, $—OCO—B—$, $—CONR^6—B—$, and $—NR^6CO—B—$, where B is a single bond or a C1-C10 alkylene group optionally containing a substituent, $R^6$ is H or a C1-C4 alkyl group optionally containing a substituent. The alkylene group more preferably contains 1 to 5 carbon atoms. $R^6$ is more preferably H or a methyl group. The symbol * indicates the bond to A in the formula.

L is preferably a single bond.

Examples of the compound include
$CH_3C(O)CH_2CH_2CH_2CH_2CH_2CH_2CH_2CH_2COOK$,
$CH_3C(O)CH_2CH_2CH_2CH_2CH_2CH_2CH_2COONa$,
$CH_3C(O)CH_2CH_2CH_2CH_2CH_2CH_2COONa$,
$CH_3C(O)CH_2CH_2CH_2CH_2CH_2COONa$,
$CH_3C(O)CH_2CH_2CH_2CH_2COONa$,
$CH_3C(O)CH_2CH_2CH_2COONa$,
$CH_3C(O)CH_2CH_2CH_2CH_2CH_2CH_2CH_2CH_2CH_2CH_2CH_2CH_2COONa$,
$CH_3C(O)CH_2CH_2CH_2CH_2CH_2CH_2CH_2CH_2CH_2CH_2CH_2CH_2CH_2CH_2CH_2CH_2COONa$
$(CH_3)_3CC(O)CH_2CH_2CH_2CH_2CH_2CH_2CH_2CH_2COONa$,
$(CH_3)_2CHC(O)CH_2CH_2CH_2CH_2CH_2CH_2CH_2CH_2COONa$,
$(CH_2)_5CHC(O)CH_2CH_2CH_2CH_2CH_2CH_2CH_2CH_2COONa$,
$CH_3CH_2C(O)CH_2CH_2CH_2CH_2CH_2CH_2CH_2COONa$,
$CH_3CH_2CH_2C(O)CH_2CH_2CH_2CH_2CH_2CH_2COONa$,
$CH_3CH_2CH_2CH_2C(O)CH_2CH_2CH_2CH_2CH_2COONa$,
$CH_3CH_2CH_2CH_2CH_2C(O)CH_2CH_2CH_2CH_2COONa$,
$CH_3CH_2CH_2CH_2CH_2CH_2C(O)CH_2CH_2CH_2COONa$,
$CH_3CH_2CH_2CH_2CH_2CH_2CH_2C(O)CH_2CH_2COONa$,
$CH_3CH_2CH_2CH_2CH_2CH_2CH_2CH_2C(O)CH_2COONa$,
$CH_3C(O)CH_2CH_2CH_2CH_2CH_2CH_2OCH_2CH_2COONa$,
$CH_3C(O)CH_2CH_2CH_2CH_2CH_2CH_2CH_2C(O)NHCH_2COOK$,
$CH_3C(O)CH_2CH_2CH_2CH_2CH_2CH_2CH_2NHC(O)CH_2COOK$,
$CH_3C(C))CH_2CH_2CH_2CH_2CH_2CH_2CH_2C(O)OCH_2COONa$,
$CH_3C(O)CH_2CH_2CH_2CH_2CH_2CH_2CH_2OC(O)CH_2COONa$,
$CH_3C(O)CH_2CH_2CH_2CH_2CH_2CH_2CH_2C(O)COONa$,
$CH_3C(O)CH_2CH_2CH_2CH_2CH_2CH_2CH_2C(O)COOH$,
$CH_3C(O)CH_2CH_2CH_2CH_2CH_2CH_2CH_2C(O)COOLi$,
$CH_3C(O)CH_2CH_2CH_2CH_2CH_2CH_2CH_2C(O)COONH_4$,
$CH_3C(O)CH_2CH_2CH_2CH_2CH_2CH_2CH_2COONa$,
$CH_3C(O)CH_2CH_2CH_2CH_2CH_2CH_2CH_2C(CH_3)_2COOK$,
$CH_3C(O)CH_2CH_2CH_2CH_2CH_2CH_2CH_2CH_2SO_3Na$,
$CH_3C(O)CH_2CH_2CH_2CH_2CH_2CH_2CH_2SO_3Na$,
$CH_3C(O)CH_2CH_2CH_2CH_2CH_2CH_2SO_3Na$,
$CH_3C(O)CH_2CH_2CH_2CH_2CH_2SO_3Na$,
$CH_3C(O)CH_2CH_2CH_2CH_2SO_3Na$,
$CH_3C(O)CH_2CH_2CH_2SO_3Na$,
$CH_3C(O)$ CH$_2$CH$_2$CH$_2$CH$_2$CH$_2$CH$_2$CH$_2$CH$_2$CH$_2$CH$_2$CH$_2$CH$_2$SO$_3$Na,
  CH$_3$C(O)
CH$_2$CH$_2$CH$_2$CH$_2$CH$_2$CH$_2$CH$_2$CH$_2$CH$_2$CH$_2$CH$_2$CH$_2$CH$_2$CH$_2$CH$_2$SO$_3$Na,
  CH$_3$C(O)
CH$_2$CH$_2$CH$_2$CH$_2$CH$_2$CH$_2$CH$_2$CH$_2$CH$_2$CH$_2$SO$_3$Na,
  (CH$_3$)$_3$CC(O)
CH$_2$CH$_2$CH$_2$CH$_2$CH$_2$CH$_2$CH$_2$CH$_2$CH$_2$SO$_3$Na,
  (CH$_3$)$_2$CHC(O)
CH$_2$CH$_2$CH$_2$CH$_2$CH$_2$CH$_2$CH$_2$CH$_2$CH$_2$SO$_3$Na, (CH$_2$)$_5$
CHC(O)CH$_2$CH$_2$CH$_2$CH$_2$CH$_2$CH$_2$CH$_2$CH$_2$CH$_2$SO$_3$Na,
  CH$_3$C(O)CH$_2$CH$_2$CH$_2$CH$_2$CH$_2$CH$_2$CH$_2$CH$_2$SO$_3$Na,
  CH$_3$C(O)CH$_2$CH$_2$CH$_2$CH$_2$CH$_2$CH$_2$CH$_2$SO$_3$Na,
  CH$_3$C(O)CH$_2$CH$_2$CH$_2$CH$_2$CH$_2$CH$_2$SO$_3$Na,
  CH$_3$C(O)CH$_2$CH$_2$CH$_2$CH$_2$CH$_2$SO$_3$Na,
  CH$_3$C(C)CH$_2$CH$_2$CH$_2$CH$_2$SO$_3$Na,
  CH$_3$C(O)CH$_2$CH$_2$CH$_2$SO$_3$Na,
  CH$_3$C(O)CH$_2$CH$_2$SO$_3$Na,
  CH$_3$C(O)CH$_2$SO$_3$Na,
  CH$_3$C(O)
CH$_2$CH$_2$CH$_2$CH$_2$CH$_2$CH$_2$CH$_2$CH$_2$CH$_2$OCH$_2$CH$_2$CH$_2$SO$_3$Na,
  CH$_3$C(O)CH$_2$CH$_2$CH$_2$CH$_2$CH$_2$CH$_2$CH$_2$CH$_2$C(O)NHCH$_2$SO$_3$Na,
  CH$_3$C(O)CH$_2$CH$_2$CH$_2$CH$_2$CH$_2$CH$_2$CH$_2$CH$_2$CH$_2$NHC(O)CH$_2$SO$_3$Na,
  CH$_3$C(O)CH$_2$CH$_2$CH$_2$CH$_2$CH$_2$CH$_2$CH$_2$CH$_2$CH$_2$C(O)SO$_3$Na,
  CH$_3$C(O)CH$_2$CH$_2$CH$_2$CH$_2$CH$_2$CH$_2$CH$_2$CH$_2$CH$_2$C(O)OCH$_2$SO$_3$Na,
  CH$_3$C(O)CH$_2$CH$_2$CH$_2$CH$_2$CH$_2$CH$_2$CH$_2$CH$_2$CH$_2$OC(O)CH$_2$SO$_3$Na,
  CH$_3$C(O)CH$_2$CH$_2$CH$_2$CH$_2$CH$_2$CH$_2$CH$_2$CH$_2$CH$_2$SO$_3$H,
  CH$_3$C(O)CH$_2$CH$_2$CH$_2$CH$_2$CH$_2$CH$_2$CH$_2$CH$_2$CH$_2$SO$_3$K,
  CH$_3$C(O)CH$_2$CH$_2$CH$_2$CH$_2$CH$_2$CH$_2$CH$_2$CH$_2$CH$_2$SO$_3$Li,
  CH$_3$C(O)
CH$_2$CH$_2$CH$_2$CH$_2$CH$_2$CH$_2$CH$_2$CH$_2$CH$_2$SO$_3$NH$_4$, and
  CH$_3$C(O)CH$_2$CH$_2$CH$_2$CH$_2$CH$_2$CH$_2$CH$_2$CH$_2$C(CH$_3$)$_2$SO$_3$Na.

The compound of the invention may suitably be produced by a production method including:

a step (11) of reacting a compound (10) represented by the following formula:

[Chem. 4]

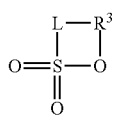

(wherein R$^1$, R$^2$, and n are defined as described above) and a sultone represented by the following formula:

[Chem. 5]

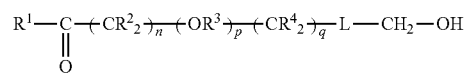

(wherein R$^3$ is defined as described above; L is a single bond, —CO$_2$—B—*, —OCO—B—*, —CONR$^6$—B—*, —NR$^6$CO—B—*, or —CO— other than the carbonyl groups in —CO$_2$—B—, —OCO—B—, —CONR$^6$—B—, and —NR$^6$CO—B—, where B is a single bond or a C1-C10 alkylene group optionally containing a substituent, R$^6$ is H or a C1-C4 alkyl group optionally containing a substituent, and * indicates the bond to —S(=O)$_2$— in the formula) to provide a compound (11) represented by the following formula:

[Chem. 6]

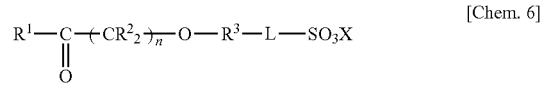

(wherein R$^1$ to R$^3$, n, and X are defined as described above; L is a single bond, —CO$_2$—B—*, —OCO—B—*, —CONR$^6$—B—*, —NR$^6$CO—B—*, or —CO— other than the carbonyl groups in —CO$_2$—B—, —OCO—B—, —CONR$^6$—B—, and —NR$^6$CO—B—, where B is a single bond or a C1-C10 alkylene group optionally containing a substituent, R$^6$ is H or a C1-C4 alkyl group optionally containing a substituent, and * indicates the bond to —SO$_3$X in the formula).

The reaction in the step (11) may be performed in the presence of a base.

Examples of the base include sodium hydride, sodium hydroxide, potassium hydroxide, and triethylamine. The base may be used in an amount of 0.5 to 20 mol relative to 1 mol of the compound (10).

The reaction in the step (11) may be performed in a solvent.

The solvent is preferably an organic solvent, more preferably an aprotic polar solvent. Examples of the organic solvent include ethers, aromatic compounds, nitriles, and halogenated hydrocarbons.

Examples of the ethers include diethyl ether, tetrahydrofuran, dioxane, and diethylene glycol diethyl ether. Diethyl ether and tetrahydrofuran are preferred.

Examples of the aromatic hydrocarbons include benzene, toluene, and xylene. Benzene is preferred.

Examples of the nitriles include acetonitrile, propionitrile, butyronitrile, isobutyronitrile, and benzonitrile. Acetonitrile is preferred.

Examples of the halogenated hydrocarbons include dichloromethane, dichloroethane, chloroform, chlorobenzene, and o-dichlorobenzene. Dichloromethane and chloroform are preferred.

The reaction temperature in the step (11) is preferably −78° C. to 150° C., more preferably −20° C. to 100° C.

The reaction pressure in the step (11) is preferably 0 to 10 MPa, more preferably 0 to 1.0 MPa.

The reaction duration in the step (11) is preferably 0.1 to 72 hours, more preferably 0.1 to 48 hours.

The compound of the invention may also suitably be produced by a production method including:

a step (21) of oxidizing a compound (20) represented by the following formula:

[Chem. 7]

(wherein R$^1$ to R$^4$, n, p, and q are defined as described above; L is a single bond, —CO$_2$—B—*, —OCO—B—*, —CONR$^6$—B—*, —NR$^6$CO—B—*, or —CO— other than the carbonyl groups in —CO$_2$—B—, —OCO—B—, —CONR$^6$—B—, and —NR$^6$CO—B—, where B is a single bond or a C1-C10 alkylene group optionally containing a substituent, $R^6$ is H or a C1-C4 alkyl group optionally containing a substituent, and * indicates the bond to —$CH_2$—OH in the formula) to provide a compound (21) represented by the following formula:

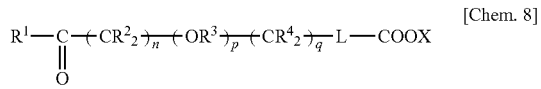
[Chem. 8]

(wherein $R^1$ to $R^4$, n, p, q, and X are defined as described above; L is a single bond, —$CO_2$—B—*, —OCO—B—*, —$CONR^6$—B—*, —$NR^6CO$—B—*, or —CO— other than the carbonyl groups in —$CO_2$—B—, —OCO—B—, —$CONR^6$—B—, and —$NR^6CO$—B—, where B is a single bond or a C1-C10 alkylene group optionally containing a substituent, $R^6$ is H or a C1-C4 alkyl group optionally containing a substituent, and * indicates the bond to —COOX in the formula).

The oxidation in the step (21) may be performed by allowing a nitrosating agent to act on the compound (20).

Examples of the nitrosating agent include sodium nitrite, nitrosylsulfuric acid, and isoamyl nitrite.

The nitrosating agent may be used in an amount of 0.5 to 10 mol relative to 1 mol of the compound (20).

The oxidation in the step (21) may be performed in a solvent. The solvent used may be trifluoroacetic acid or acetonitrile, for example.

The oxidation temperature in the step (21) is preferably −78° C. to 200° C., more preferably −20° C. to 100° C.

The oxidation pressure in the step (21) is preferably 0 to 10 MPa, more preferably 0 to 1.0 MPa.

The oxidation duration in the step (21) is preferably 0.1 to 72 hours, more preferably 0.1 to 24 hours.

The compound (10) and the compound (20) each may be produced by a production method including:

a step (101) of hydroxylating a compound (100) represented by the following formula:

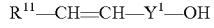

(wherein $R^{11}$ is H, a linear or branched alkyl group containing one or more carbon atoms and optionally containing a substituent, or a cyclic alkyl group containing three or more carbon atoms and optionally containing a substituent, and optionally contains a monovalent or divalent heterocycle or optionally forms a ring when containing three or more carbon atoms; and $Y^1$ is —$(CR^2_2)_n$— or —$(CR^2_2)_n$—$(OR^3)_p$—$(CR^4_2)_q$-L-$CH_2$—, where $R^2$ to $R^4$, n, L, p, and q are defined as described above) to provide a compound (101) represented by the following formula:

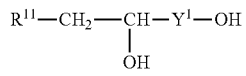
[Chem. 9]

(wherein $R^{11}$ and $Y^1$ are defined as described above); and a step (102) of oxidizing the compound (101) to provide a compound (102) represented by the following formula:

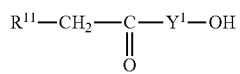
[Chem. 10]

(wherein $R^{11}$ and $Y^1$ are defined as described above).

The alkyl group for $R^{11}$ is preferably free from a carbonyl group.

In the alkyl group for $R^{11}$, 75% or less of the hydrogen atoms binding to any of the carbon atoms may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group preferably contains no substituent.

$R^{11}$ is preferably H, a C1-C9 linear or branched alkyl group optionally containing a substituent, or a C3-C9 cyclic alkyl group optionally containing a substituent, more preferably H, a C1-C9 linear or branched alkyl group free from a carbonyl group, or a C3-C9 cyclic alkyl group free from a carbonyl group, still more preferably H or a C1-C9 linear or branched alkyl group free from a substituent, further more preferably H, a methyl group (—$CH_3$), or an ethyl group (—$C_2H_5$), particularly preferably H or a methyl group (—$CH_3$), most preferably H.

The hydroxylation in the step (101) may be performed by a method (1) in which iron(II) phthalocyanine (Fe(Pc)) and sodium borohydride are allowed to act on the compound (100) in an oxygen atmosphere or a method in which isopinocampheylborane (IpcBH$_2$) is allowed to act on the compound (100) and then the resulting intermediate (dialkyl borane) is oxidized.

In the method (1), iron(II) phthalocyanine may be used in a catalytic amount, and may be used in an amount of 0.001 to 1.2 mol relative to 1 mol of the compound (100).

In the method (1), sodium borohydride may be used in an amount of 0.5 to 20 mol relative to 1 mol of the compound (100).

The reaction in the method (1) may be performed in a solvent. The solvent is preferably an organic solvent, such as an ether, a halogenated hydrocarbon, an aromatic hydrocarbon, a nitrile, or a nitrogen-containing polar organic compound.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

Examples of the nitrile include acetonitrile, propionitrile, butyronitrile, isobutyronitrile, and benzonitrile. Acetonitrile is preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

The reaction temperature in the method (1) is preferably −78° C. to 200° C., more preferably 0° C., to 150° C.

The reaction pressure in the method (1) is preferably 0 to 5.0 MPa, more preferably 0.1 to 1.0 MPa.

The reaction duration in the method (1) is preferably 0.1 to 72 hours, more preferably 0.1 to 48 hours.

In the method (2), isopinocampheylborane may be used in an amount of 1.0 to 10.0 mol relative to 1 mol of the compound (100).

The reaction of the compound (100) and isopinocampheylborane may be performed in a solvent. The solvent is preferably an organic solvent, such as an ether, a halogenated hydrocarbon, or an aromatic hydrocarbon.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

The temperature of the reaction of the compound (100) and isopinocampheylborane is preferably −78° C. to 200° C., more preferably 0° C. to 150° C.

The pressure of the reaction of the compound (100) and isopinocampheylborane is preferably 0 to 5.0 MPa, more preferably 0.1 to 1.0 MPa.

The duration of the reaction of the compound (100) and isooinocampheylborane is preferably 0.1 to 72 hours, more preferably 0.1 to 48 hours.

The oxidation in the method (2) may be performed by allowing an oxidizing agent to act on the intermediate. An example of the oxidizing agent is hydrogen peroxide. The oxidizing agent may be used in an amount of 0.7 to 10 mol relative to 1 mol of the intermediate.

The oxidation in the method (2) may be performed in a solvent. Examples of the solvent include water, methanol, and ethanol. Water is preferred.

The oxidation temperature in the method (2) is preferably 0° C. to 100° C. more preferably 0° C. to 80° C.

The oxidation pressure in the method (2) is preferably 0 to 5.0 MPa, more preferably 0.1 to 1.0 MPa.

The oxidation duration in the method (2) is preferably 0.1 to 72 hours, more preferably 0.1 to 48 hours.

The oxidation of the compound (101) in the step (102) may be performed by, for example, (a) a method using the Jones reagent ($CrO_3/H_2SO_4$) (Jones oxidation), (b) a method using Less-Martin periodinane (DMP) (Dess-Martin oxidation), (c) a method using pyridinium chlorochromate (PCC), (d) a method of allowing a bleaching agent (about 5% to 6% aqueous solution of NaOCl) to act in the presence of a nickel compound such as $NiCl_2$, or (e) a method of allowing a hydrogen acceptor such as an aldehyde or a ketone to act in the presence of an aluminum catalyst such as $Al(CH_3)_3$ or $Al[OCH(CH_3)_2]_3$ (Oppenauer oxidation).

The oxidation in the step (102) may be performed in a solvent. The solvent is preferably any of water and organic solvents, such as water, ketones, ethers, halogenated hydrocarbons, aromatic hydrocarbons, and nitriles.

Examples of the ketones include acetone, methyl ethyl ketone, methyl isobutyl ketone, cyclohexanone, and diacetone alcohol. Acetone is preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the aromatic hydrocarbons include benzene, toluene, and xylene. Benzene and toluene are preferred.

Examples of the nitriles include acetonitrile, propionitrile, butyronitrile, isobutyronitrile, and benzonitrile. Acetonitrile is preferred.

The oxidation temperature in the step (102) is preferably −78° C. to 200° C., and may appropriately be selected in accordance with the method used.

The oxidation pressure in the step (102) is preferably 0 to 5.0 MPa, and may appropriately be selected in accordance with the method used.

The oxidation duration in the step (102) is preferably 0.1 to 72 hours, and may appropriately be selected in accordance with the method used.

The compound (10) and the compound (20) each may also be produced by a production method including:

a step (201) of ozonolyzing a compound (200) represented by the following formula:

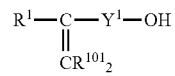

[Chem. 11]

(wherein $R^1$ and $Y^1$ are defined as described above; and $R^{101}$ is an organic group) to provide a compound (201) represented by the following formula:

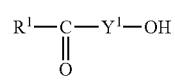

[Chem. 12]

(wherein $R^1$ and $Y^1$ are defined as described above).

$R^{101}$s are each preferably a C1-C20 alkyl group. The two $R^{101}$s are the same as or different from each other.

The ozonolysis in the step (201) may be performed by allowing ozone to act on the compound (200), followed by post-treatment with a reducing agent.

The ozone may be generated by dielectric barrier discharge in oxygen gas.

Examples of the reducing agent used in the post-treatment include zinc, dimethyl sulfide, thiourea, and phosphines. Phosphines are preferred.

The ozonolysis in the step (201) may be performed in a solvent. The solvent is preferably any of water and organic solvents, such as water, alcohols, carboxylic acids, ethers, halogenated hydrocarbons, and aromatic hydrocarbons.

Examples of the alcohols include methanol, ethanol, 1-propanol, and isopropanol. Methanol and ethanol are preferred.

Examples of the carboxylic acids include acetic acid and propionic acid. Acetic acid is preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the aromatic hydrocarbons include benzene, toluene, and xylene. Benzene and toluene are preferred.

The ozonolysis temperature in the step (201) is preferably −78° C. to 200° C., more preferably 0° C. to 150° C.

The ozonolysis pressure in the step (201) is preferably 0 to 5.0 MPa, more preferably 0.1 to 1.0 MPa.

The ozonolysis duration in the step (201) is preferably 0.1 to 72 hours, more preferably 0.1 to 48 hours.

The compound (10) and the compound (20) each may also be produced by a production method including:

a step (301) of epoxidizing a compound (300) represented by the following formula:

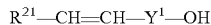

R²¹—CH=CH—Y¹—OH (wherein Y¹ is defined as described above; R²¹ is H, a linear or branched alkyl group containing one or more carbon atoms and optionally containing a substituent, or a cyclic alkyl group containing three or more carbon atoms and optionally containing a substituent, and optionally contains a monovalent or divalent heterocycle or optionally forms a ring when containing three or more carbon atoms) to provide a compound (301) represented by the following formula:

[Chem. 13]

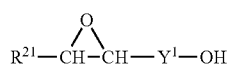

(wherein R²¹ and Y¹ are defined as described above);

a step (302) of reacting the compound (301) with a dialkylcopper lithium represented by R²²₂CuLi (wherein R²² is a linear or branched alkyl group containing one or more carbon atoms and optionally containing a substituent or a cyclic alkyl group containing three or more carbon atoms and optionally containing a substituent, and optionally contains a monovalent or divalent heterocycle or optionally forms a ring when containing three or more carbon atoms) to provide a compound (302) represented by the following formula:

[Chem. 14]

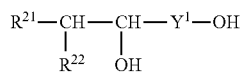

(wherein R²¹, R²², and Y¹ are defined as described above); and a step (303) of oxidizing the compound (302) to provide a compound (303) represented by the following formula:

[Chem. 15]

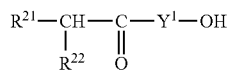

(wherein R²¹, R²², and Y¹ are defined as described above).

The alkyl group for R²¹ is preferably free from a carbonyl group.

In the alkyl group for R²¹, 75% or less of the hydrogen atoms binding to any of the carbon atoms may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group preferably contains no substituent.

R²¹ is preferably H, a C1-C8, linear or branched alkyl group optionally containing a substituent, or a C3-C8 cyclic alkyl group optionally containing a substituent, more preferably H, a C1-C8 linear or branched alkyl group free from a carbonyl group, or a C3-C8 cyclic alkyl group free from a carbonyl group, still more preferably H or a C1-C8 linear or branched alkyl group free from a substituent, particularly preferably H or a methyl group (—CH₃), most preferably H.

The alkyl group for R²² is preferably free from a carbonyl group.

In the alkyl group for R²², 75% or less of the hydrogen atoms binding to any of the carbon atoms may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group preferably contains no substituent.

R²² is preferably a C1-C9 linear or branched alkyl group optionally containing a substituent or a C3-C9 cyclic alkyl group optionally containing a substituent, more preferably a C1-C9 linear or branched alkyl group free from a carbonyl group or a C3-C9 cyclic alkyl group free from a carbonyl group, still more preferably a C1-C9 linear or branched alkyl group free from a substituent, particularly preferably a methyl group (—CH₃) or an ethyl group (—C₂H₅), most preferably a methyl group (—CH₃).

Two R²²s are the same as or different from each other.

R²¹ and R²² preferably contain 1 to 7 carbon atoms, more preferably 1 or 2 carbon atoms, most preferably 1 carbon atom, in total.

The epoxidation in the step (301) may be performed by allowing an epoxidizing agent to act on the compound (300).

Examples of the epoxidizing agent include peroxy acids such as meta-chloroperbenzoic acid (m-CPBA), perbenzoic acid, hydrogen peroxide, and tert-butyl hydroperoxide, dimethyl dioxolane, and methyl trifluoromethyl dioxolane. Peroxy acids are preferred, and meta-chloroperbenzoic acid is more preferred.

The epoxidizing agent may be used in an amount of 0.5 to 10.0 mol relative to 1 mol of the compound (300).

The epoxidation in the step (301) may be performed in a solvent. The solvent is preferably an organic solvent, such as a ketone, an ether, a halogenated hydrocarbon, an aromatic hydrocarbon, a nitrile, pyridine, a nitrogen-containing polar organic compound, or dimethyl sulfoxide. Dichloromethane is preferred.

Examples of the ketone include acetone, methyl ethyl ketone, methyl isobutyl ketone, cyclohexanone, and diacetone alcohol. Acetone is preferred.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

Examples of the nitrile include acetonitrile, propionitrile, butyronitrile, isobutyronitrile, and benzonitrile. Acetonitrile is preferred.

Examples of the nitrogen-containing polar organic compounds include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

The epoxidation temperature in the step (301) is preferably −78° C. to 200° C., more preferably −40° C. to 150° C., The epoxidation pressure in the step (301) is preferably 0 to 5.0 MPa, more preferably 0.1 to 1.0 MPa.

The epoxidation duration in the step (301) is preferably 0.1 to 72 hours, more preferably 0.1 to 48 hours.

In the step (302), the dialkylcopper lithium may be used in an amount of 0.5 to 10.0 mol relative to 1 mol of the compound (301).

The reaction in the step (302) may be performed in a solvent. The solvent is preferably an organic solvent, such as an ether, a halogenated hydrocarbon, or an aromatic hydrocarbon.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

The reaction temperature in the step (302) is preferably −78° C. to 200° C., more preferably −40° C. to 150° C.

The reaction pressure in the step (302) is preferably 0 to 5.0 MPa, more preferably 0.1 to 1.0 MPa.

The reaction duration in the step (302) is preferably 0.1 to 72 hours, more preferably 0.1 to 48 hours.

The oxidation of the compound (302) in the step (303) may be performed by, for example, (a) a method of using the Jones reagent ($CrO_3/H_2SO_4$) (Jones oxidation), (b) a method of using Dess-Martin periodinane (DMP) (mess-Martin oxidation), (c) a method of using pyridinium chlorochromate (PCC), (d) a method of allowing a bleaching agent (about 5% to 6% aqueous solution of NaOCl) to act in the presence of a nickel compound such as $NiCl_2$, or (e) a method of allowing a hydrogen acceptor such as an aldehyde or a ketone to act in the presence of an aluminum catalyst such as $Al(CH_3)_3$ or $Al[OCH(CH_3)_2]_3$ (Oppenauer oxidation).

The oxidation in the step (303) may be performed in a solvent. The solvent is preferably any of water and organic solvents, such as water, ketones, alcohols, ethers, halogenated hydrocarbons, aromatic hydrocarbons, and nitriles.

Examples of the ketones include acetone, methyl ethyl ketone, methyl isobutyl ketone, cyclohexanone, and diacetone alcohol. Acetone is preferred.

Examples of the alcohols include methanol, ethanol, 1-propanol, and isopropanol. Methanol and ethanol are preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the aromatic hydrocarbons include benzene, toluene, and xylene. Benzene and toluene are preferred.

Examples of the nitriles include acetonitrile, propionitrile, butyronitrile, isobutyronitrile, and benzonitrile. Acetonitrile is preferred.

The oxidation temperature in the step (303) is preferably −78° C. to 200° C., and may appropriately be selected in accordance with the method used.

The oxidation pressure in the step (303) is preferably 0 to 5.0 MPa, and may appropriately be selected in accordance with the method used.

The oxidation duration in the step (303) is preferably 0.1 to 72 hours, and may appropriately be selected in accordance with the method used.

The compound (10) and the compound (20) each may also be produced by a production method including:

a step (401) of oxidizing a compound (100) represented by the following formula:

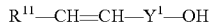

(wherein $R^{11}$ and $Y^1$ are defined as described above) to provide a compound (401) represented by the following formula:

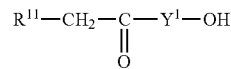

[Chem. 16]

(wherein $R^{11}$ and $Y^1$ are defined as described above).

The oxidation in the step (401) may be performed by allowing an oxidizing agent to act on the compound (100) in the presence of water and a palladium compound.

Examples of the oxidizing agent include monovalent or divalent copper salts such as copper chloride, copper acetate, copper cyanide, and copper trifluoromethanethiolate, iron salts such as iron chloride, iron acetate, iron cyanide, iron trifluoromethanethiolate, hexacyanoferrates, and iron sulfate, benzoquinones such as 1,4-benzoquinone, 2,3-dichloro-5,6-dicyano-1,4-benzoquinone, tetrachloro-1,2-benzoquinone, and tetrachloro-1,4-benzoquinone, $H_2O_2$, $MnO_2$, $KMnO_4$, $RuO_4$, m-chloroperbenzoic acid, peracetic acid, perbenzoic acid, tert-butyl hydroperoxide, cumene hydroperoxide, potassium persulfate, mixtures of potassium hydrogen persulfate-potassium hydrogen sulfate-potassium sulfate, and oxygen. Copper salts, iron salts, benzoquinones, mixtures of potassium hydrogen persulfate-potassium hydrogen sulfate-potassium sulfate, and oxygen are preferred, and copper chloride, iron chloride, 1,4-benzoquinone, and oxygen are more preferred.

The oxidizing agent may be used in an amount of 0.001 to 10 mol relative to 1 mol of the compound (100).

The water may be used in an amount of 0.5 to 1000 mol relative to 1 mol of the compound (100).

An example of the palladium compound is palladium dichloride. The palladium compound may be used in a catalytic amount, and may be used in an amount of 0.0001 to 1.0 mol relative to 1 mol of the compound (100).

The oxidation in the step (401) may be performed in a solvent. Examples of the solvent include water, esters, aliphatic hydrocarbons, aromatic hydrocarbons, alcohols, carboxylic acids, ethers, halogenated hydrocarbons, nitrogen-containing polar organic compounds, nitriles, dimethyl sulfoxide, and sulfolane.

Examples of the esters include ethyl acetate, butyl acetate, ethylene glycol monomethyl ether acetate, and propylene glycol monomethyl ether acetate (PGMEA, also known as 1-methoxy-2-acetoxypropane). Ethyl acetate is preferred.

Examples of the aliphatic hydrocarbons include hexane, cyclohexane, heptane, octane, nonane, decane, undecane, dodecane, and mineral spirits. Cyclohexane and heptane are preferred.

Examples of the aromatic hydrocarbons include benzene, toluene, and xylene. Benzene and toluene are preferred.

Examples of the alcohols include methanol, ethanol, 1-propanol, and isopropanol.

Examples of the carboxylic acids include acetic acid and propionic acid. Acetic acid is preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the nitrogen-containing polar organic compounds include N,N-dimethylformamide, N,N-dimethylacetamide, 4-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

Examples of the nitriles include acetonitrile, propionitrile, butyronitrile, isobutyronitrile, and benzonitrile. Acetonitrile is preferred.

The oxidation temperature in the step (401) is preferably −78° C. to 200° C., more preferably −20° C. to 150° C.

The oxidation pressure in the step (401) is preferably 0 to 10 MPa, more preferably 0.1 to 5.0 MPa.

The oxidation duration in the step (401) is preferably 0.1 to 72 hours, more preferably 0.1 to 48 hours.

The compound of the invention may also be produced by a production method including:

a step (31) of oxidizing a compound (30) represented by the following formula:

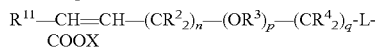
COOX (wherein $R^2$ to $R^4$, $R^{11}$, n, p, q, and X are defined as described above; L is a single bond, —$CO_2$—B—*, —OCO—B—*, —$CONR^6$—B—*, —$NR^6CO$—B—*, or —CO— other than the carbonyl groups in —$CO_2$—B—, —OCO—B—, —$CONR^6$—B—, and —$NR^6CO$—B—, where B is a single bond or a C1-C10 alkylene group optionally containing a substituent, $R^6$ is H or a C1-C4 alkyl group optionally containing a substituent, and * indicates the bond to —COOX in the formula) to provide a compound (31) represented by the following formula:

[Chem. 17]
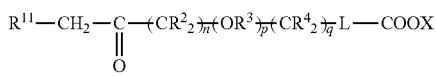

(wherein $R^2$ to $R^4$, L, $R^{11}$, n, p, q, and X are defined as described above).

The oxidation in the step (31) may be performed by allowing an oxidizing agent to act on the compound (30) in the presence of water and a palladium compound under the same conditions as in the oxidation in the step (401).

The compound of the invention may also be produced by a production method including:

a step (41) of oxidizing a compound (40) represented by the following formula:

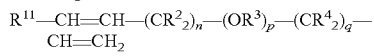

(wherein $R^2$ to $R^4$, $R^{11}$, n, p, and q are defined as described above) to provide a compound (41) represented by the following formula:

[Chem. 18]
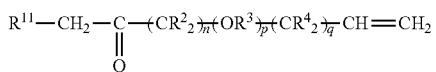

(wherein $R^2$ to $R^4$, $R^{11}$, n, p, and q are defined as described above); and a step (42) of reacting the compound (41) with sodium hydrogen subsulfide to provide a compound (42) represented by the following formula:

[Chem. 19]
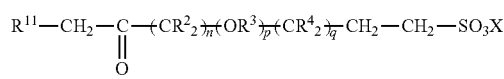

(wherein $R^2$ to $R^4$, $R^{11}$, a, p, q, and X are defined as described above).

The oxidation in the step (41) may be performed by allowing an oxidizing agent to act on the compound (40) in the presence of water and a palladium compound under the same conditions as in the oxidation in the step (401).

In the step (42), the sodium hydrogen subsulfide may be used in an amount of 0.001 to 20 mol relative to 1 mol of the compound (41).

The reaction in the step (42) may be performed in the presence of azobisisobutyronitrile (AIBN).

The azobisisobutyronitrile may be used in an amount of 0.5 to 20 mol relative to 1 mol of the compound (41).

The reaction in the step (42) may be performed in a solvent.

The solvent is preferably an organic solvent, more preferably an aprotic polar solvent. Examples of the organic solvent include ethers, aromatic compounds, nitriles, and halogenated hydrocarbons.

Examples of the ethers include diethyl ether, tetrahydrofuran, dioxane, and diethylene glycol diethyl ether. Diethyl ether and tetrahydrofuran are preferred.

Examples of the aromatic hydrocarbons include benzene, toluene, and xylene. Benzene is preferred.

Examples of the nitriles include acetonitrile, propionitrile, butyronitrile, isobutyronitrile, and benzonitrile. Acetonitrile is preferred.

Examples of the halogenated hydrocarbons include dichloromethane, dichloroethane, chloroform, chlorobenzene, and o-dichlorobenzene. Dichloromethane and chloroform are preferred.

The reaction temperature in the step (42) is preferably −78° C. to 150° C., more preferably −20° C. to 100° C.

The reaction pressure in the step (42) is preferably 0 to 10 MPa, more preferably 0 to 1.0 MPa.

The reaction duration in the step (42) is preferably 0.1 to 72 hours, more preferably 0.1 to 48 hours.

The compound of the invention may also be produced by a production method including:

a step (51) of reacting a compound (50) represented by the following formula:

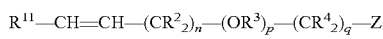

(wherein $R^2$ to $R^4$, $R^{11}$, n, p, and q are defined as described above; and Z is fluorine, chlorine, bromine, or iodine) with a compound (50-1) represented by the following formula:

[Chem. 20]
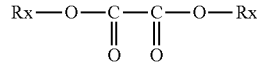

(wherein Rx is a C1-C10 linear or branched alkyl group) to provide a compound (51) represented by the following formula:

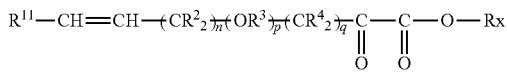
[Chem. 21]

(wherein $R^2$ to $R^4$, $R^{11}$, Rx, n, p, and q are defined as described above);

a step (52) of oxidizing the compound (51) to provide a compound (52) represented by the following formula:

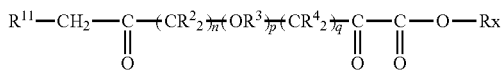
[Chem. 22]

(wherein $R^2$ to $R^4$, $R^{11}$, Rx, n, p, and q are defined as described above); and a step (53) of hydrolyzing the compound (52) to provide a compound (53) represented by the following formula:

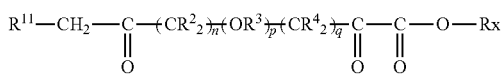
[Chem. 23]

(wherein $R^2$ to $R^4$, $R^{11}$, Rx, n, p, and q are defined as described above).

The reaction in the step (51) may be performed in the presence of a metal such as magnesium.

The metal may be used in an amount of 0.5 to 20 mol relative to 1 mol of the compound (50).

The reaction in the step (52) may be performed in a solvent. Examples of the solvent include water, esters, aliphatic hydrocarbons, aromatic hydrocarbons, alcohols, carboxylic acids, ethers, halogenated hydrocarbons, nitrogen-containing polar organic compounds, nitriles, dimethyl sulfoxide, and sulfolane.

Examples of the esters include ethyl acetate, butyl acetate, ethylene glycol monomethyl ether acetate, and propylene glycol monomethyl ether acetate (PGMEA, also known as 1-methoxy-2-acetoxypropane). Ethyl acetate is preferred.

Examples of the aliphatic hydrocarbons include hexane, cyclohexane, heptane, octane, nonane, decane, undecane, dodecane, and mineral spirits. Cyclohexane and heptane are preferred.

Examples of the aromatic hydrocarbons include benzene, toluene, and xylene. Benzene and toluene are preferred.

Examples of the alcohols include methanol, ethanol, 1-propanol, and isopropanol.

Examples of the carboxylic acids include acetic acid and propionic acid. Acetic acid is preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the nitrogen-containing polar organic compounds include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

Examples of the nitriles include acetonitrile, propionitrile, butyronitrile, isobutyronitrile, and benzonitrile. Acetonitrile is preferred.

The reaction temperature in the step (52) is preferably −78° C. to 150° C., more preferably −20° C. to 100° C.

The reaction pressure in the step (52) is preferably 0 to 10 MPa, more preferably 0 to 1.0 MPa.

The reaction duration in the step (52) is preferably 0.1 to 72 hours, more preferably 0.1 to 48 hours.

The oxidation in the step (52) may be performed by allowing an oxidizing agent to act on the compound (51) in the presence of water and a palladium compound under the same conditions as in the oxidation in the step (401).

The hydrolysis in the step (53) may be performed by a known method. For example, the hydrolysis may be performed by allowing a sodium hydroxide aqueous solution to act on the compound.

The compound of the invention may also be produced by a production method including:

a step (61) of reacting a compound (60) represented by the following formula:

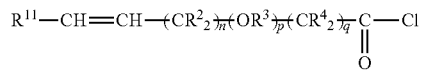
[Chem. 24]

(wherein $R^2$ to $R^4$, $R^{11}$, n, p, and q are defined as described above) with glycine to provide a compound (61) represented by the following formula:

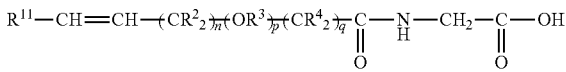
[Chem. 25]

(wherein $R^2$ to $R^4$, $R^{11}$, n, p, and q are defined as described above); and a step (62) of oxidizing the compound. (61) to provide a compound (62) represented by the following formula:

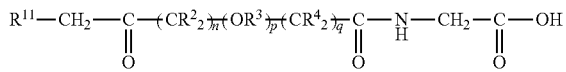
[Chem. 26]

(wherein $R^2$ to $R^4$, $R^{11}$, n, p, and q are defined as described above).

The reaction in the step (61) may be performed in the presence of a base.

Examples of the base include sodium hydride, sodium hydroxide, potassium hydroxide, and triethylamine. The base may be used in an amount of 0.5 to 20 mol relative to 1 mol of the compound (10).

The reaction in the step (61) may be performed in a solvent. Examples of the solvent include water, esters, aliphatic hydrocarbons, aromatic hydrocarbons, alcohols, carboxylic acids, ethers, halogenated hydrocarbons, nitrogen-containing polar organic compounds, nitriles, dimethyl sulfoxide, and sulfolane.

Examples of the esters include ethyl acetate, butyl acetate, ethylene glycol monomethyl ether acetate, and propylene glycol monomethyl ether acetate (PGMEA, also known as 1-methoxy-2-acetoxypropane). Ethyl acetate is preferred.

Examples of the aliphatic hydrocarbons include hexane, cyclohexane, heptane, octane, nonane, decane, undecane, dodecane, and mineral spirits. Cyclohexane and heptane are preferred.

Examples of the aromatic hydrocarbons include benzene, toluene, and xylene. Benzene and toluene are preferred.

Examples of the alcohols include methanol, ethanol, 1-propanol, and isopropanol.

Examples of the carboxylic acids include acetic acid and propionic acid. Acetic acid is preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the nitrogen-containing polar organic compounds include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

Examples of the nitriles include acetonitrile, propionitrile, butyronitrile, isobutyronitrile, and benzonitrile. Acetonitrile is preferred.

The reaction temperature in the step (61) is preferably −78° C. to 150° C., more preferably −20° C. to 100° C.

The reaction pressure in the step (61) is preferably 0 to 10 MPa, more preferably 0 to 1.0 MPa.

The reaction duration in the step (61) is preferably 0.1 to 72 hours, more preferably 0.1 to 48 hours.

The oxidation in the step (62) may be performed by allowing an oxidizing agent to act on the compound (61) in the presence of water and a palladium compound under the same conditions as in the oxidation in the step (401).

In each of the above production methods, the resulting compounds may be subjected to any of evaporation of a solvent or operations such as distillation and purification after the respective steps, whereby the purity of each compound may be increased. When the resulting compound is a compound in which X is H, i.e., containing —$SO_3H$ or —COOH, the compound may be brought into contact with an alkali such as sodium carbonate or ammonia so that such a group is converted into a salt form.

EXAMPLES

The invention is described with reference to examples, but the invention is not intended to be limited by these examples.

Example 1

A flask was charged with 11-hydroxyundecan-2-one (1.86 g) and THF, and the components were stirred at 0° C. Thereto was added gradually 60% NaH (0.4 g), and the components were then stirred for 30 minutes. A solution of propanesultone (1.22 g) in THF was gradually dropwise added thereto, and the components were then stirred at 40° C. for 10 hours. Diethyl ether was added thereto and the mixture was filtered, whereby 1.65 g (yield: 50%) of the target sodium 3-((10-oxoundecyl)oxy)propane-1-sulfonate was obtained.

Example 2

A mixture of 10-undecenoic acid (4.7 g), 1,4-benzoquinone (0.63 g), DMF (50 mL), water (5 mL), and $PdCl_2$ (0.09 g) was heated and stirred at 90° C. for 12 hours.

The solvent was then evaporated under reduced pressure. The resulting residue was mixed with a solution of sodium methoxide in methanol and the mixture was filtered. The solid residue was mixed with hydrochloric acid and the mixture was extracted with ethyl acetate. The extract was dried over sodium sulfate, and the solvent was evaporated under reduced pressure. The residue was purified by column chromatography, whereby 10-oxoundecanoic acid (3.2 g) was obtained.

The spectrum data of the resulting 10-oxoundecanoic acid are the following.

$^1$H-NMR (CDCl$_3$) δppm: 1.27-1.37 (m, 8H), 1.51-1.60 (m, 4H), 2.11 (s, 3H), 2.29-2.42 (m, 4H)

The resulting 10-oxoundecanoic acid (0.73 g) was added to a 2 M solution of ammonia in methanol and water was evaporated. Thereby, ammonium 10-oxoundecanoate (0.57 g) was obtained.

The spectrum data of the resulting ammonium 10-oxoundecanoate are the following.

$^1$H-NMR (CDCl$_3$) δppm: 1.05 (m, 8H), 1.31 (m, 4H), 1.96-2.02 (m, 5H), 2.28-2.34 (t, J=7.3, 4H)

Example 3

To 10-oxoundecanoic acid (1.8 g) was added 1.0 M KOH water and water was then evaporated, whereby potassium 10-oxoundecanoate (2.2 g) was obtained.

The spectrum data of the resulting potassium 10-oxoundecanoate are the following.

$^1$H-NMR (CDCl$_3$) δppm: 1.04 (m, 8H), 1.30-1.32 (m, 4H), 1.89-2.01 (m, 5H), 2.27-2.33 (t, J=7.6, 4H)

Example 4

A reactor was charged with 1,10-undecadiene (6.55 g), dimethyl formamide (300 ml), water (43 ml), palladium chloride (0.38 g), and iron(III) sulfate n-hydrate (25.8 g), and the components were heated and stirred at 45° C. The mixture was subjected to liquid separation, dehydration, concentration, and silica gel column chromatography purification, whereby 10-undecen-2-one (3.17 g) was obtained at a yield of 44%.

Next, a reactor was charged with 10-undecen-2-one (1.29 g), methanol (54 ml), water (27 ml), sodium hydrogen sulfite (1.07 g), and azobisisobutyronitrile (0.13 g), and the components were heated and stirred at 80° C. The resulting reaction mixture was recrystallized, whereby sodium 10-oxoundecanesulfonate (0.41 g) was obtained at a yield of 19%.

Example 5

Sodium 11-oxododecanesulfonate was synthesized in the same manner as in Example 1, except that the material was changed from 1,10-undecadiene to 1,11-dodecadiene.

Example 6

A reactor was charged with magnesium (flakes, 8.32 g, 342.1 mmol) and THF (20 mL), and 11-bromoundecene (11.95 g, 102.6 mmol) diluted with THF (100 mL) was slowly dropwise added thereto. The components were then heated up to 70° C. The reaction solution was dropwise added to a solution mixture of diethyl oxalate (10.0 g, 68.4 mmol) and THF (70 mL) cooled at −78° C. The mixture was warmed up to room temperature, and a saturated ammonium chloride aqueous solution (150 mL) was added for quenching. The mixture was subjected to liquid separation, dehydration, concentration, and silica gel column chromatography purification, whereby 8.07 g (yield: 46.3%) of ethyl 2-oxotridec-12-enoate (colorless, transparent liquid) was obtained.

A reactor was charged with ethyl 2-oxotridec-12-enoate (8.62 g, 33.9 mmol), DMAc (20 mL), deionized water (2.0 mL), benzoquinone (3.66 g, 33.9 mmol), and $PdCl_2$ (30.0 mg, 0.169 mmol), and the components were heated and stirred at 40° C. The mixture was subjected to liquid separation, dehydration, concentration, and silica gel column chromatography purification, whereby 4.54 g (4.54 g) of ethyl 2,12-dioxotridecanoate was obtained at a yield of 50%.

A reactor was charged with ethyl 2,12-dioxotridecanoate (3.63 g, 13.4 mmol) and 1.0 M HCl aqueous solution (50 mL), and the components were heated and stirred at 110° C. The mixture was subjected to liquid separation, dehydration, and concentration, whereby 2,12-dioxotridecanoic acid (3.17 g) was obtained. A 1.0 M NaOH aqueous solution was allowed to act thereon, whereby sodium 2,12-dioxotridecanoate was obtained at a quantitative yield.

Example 7

A reactor was charged with glycine (3.2 g) and sodium hydroxide aqueous solution (85 mL). A solution of 10-undecenoyl chloride (5.7 g) in THF was dropwise added under stirring at 0° C., and the mixture was further stirred at room temperature. The reaction completion was followed by quenching with hydrochloric acid. The product was purified by liquid separation and recrystallization, whereby 2-(10-undecenamide)acetic acid (4.8 g) was obtained at a yield of 71%.

A mixture of 2-(10-undecenamide)acetic acid (4.8 g), N,N-dimethylacetamide (80 mL), water (8.0 mL), and $PdCl_2$ (0.18 g) was heated and stirred in a reactor in an oxygen atmosphere (0.1 MPa) at 80° C. for 24 hours. After the reaction was completed, the product was purified by liquid separation and recrystallization, whereby 2-(10-oxoundecanamide)acetic acid (1.5 g) was obtained at a yield of 29%.

To a solution of this 2-(10-oxoundecanamide)acetic acid (1.5 g) in a mixture of ethanol/water was dropwise added a 0.5 M solution (11 mL) of KOH in ethanol. The mixture was stirred, and the solvent was then evaporated at room temperature under reduced pressure. Thereby, potassium 2-(10-oxoundecanamide)acetate (1.8 g) was obtained in the form of white solid.

Sodium 3-((10-oxoundecyl)oxy)propane-1-sulfonate obtained in Example 1, ammonium 10-oxoundecanoate obtained in Example 2, potassium 10-oxoundecanoate obtained in Example 3, sodium 10-oxoundecanesulfonate obtained in Example 4, sodium 11-oxododecanesulfonate obtained in Example 5, sodium 2,12-dioxotridecanoate obtained in Example 6, and potassium 2-(10-oxoundecanamide)acetate obtained in Example 7 were each dissolved in water so as to have the concentration shown in Table 1, and the surface tension was measured. The surface tension was measured by the Wilhelmy method at 20° C. The results are shown in Table 1.

TABLE 1

|  |  | Amount of compound relative to water (wt %) | | |
|---|---|---|---|---|
|  |  | 0.01 | 0.1 | 1.0 |
| Surface tension (mN/m) | Example 1 | 72.1 | 63.0 | 46.8 |
|  | Example 2 | 72.0 | 60.0 | 58.8 |
|  | Example 3 | 71.2 | 70.1 | 64.0 |
|  | Example 4 | 71.5 | 57.3 | 33.7 |
|  | Example 5 | 69.0 | 55.0 | 31.0 |
|  | Example 6 | 74.5 | 55.6 | Insoluble and unmeasured |
|  | Example 7 | 76.6 | 75.8 | 71.1 |

INDUSTRIAL APPLICABILITY

The compound of the invention can suitably reduce the surface tension of water.

The compound of the invention can suitably be used as a surfactant.

The compound of the invention can suitably be used as a surfactant accelerator particularly as a surfactant accelerator in coating material, lacquer, adhesive, or the like).

The compound of the invention can suitably be used as a viscosity reducer, for example.

The compound of the invention can suitably be used as a dispersant, particularly an aqueous dispersant, for example.

The compound of the invention can suitably be used as an emulsifier, for example.

The invention claimed is:
1. A compound represented by the following formula:

[Chem. 1]

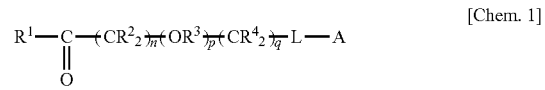

wherein
$R^1$ is a methyl group;
$R^2$ and $R^4$ are each individually H or a substituent, wherein the substituent is selected from the group consisting of a halogen atom, a C1-C10 linear or branched alkyl group, a C3-C10 cyclic alkyl group and a hydroxyl group;
$R^3$ is a C1-C10 alkylene group;
n is an integer of 1 or greater;
p and q are each individually an integer of 0 or greater;
a sum of n, p, and q is an integer of 8 or greater;
A is —$SO_3X$ or —COOX, wherein X is $NR^5_4$, imidazolium, or phosphonium, where $R^5$s are each H or a non-substituted alkyl group and are the same as or different from each other and at least one $R^5$ among four of $R^5$s is H; and
L is a single bond, —$CO_2$—B—*, —OCO—B—*, —$CONR^6$—B—*, —$NR^6CO$—B—*, or —CO—, where B is a single bond or a C1-C10 alkylene group, $R^6$ is H or a C1-C4 alkyl group, and * indicates the bond to A in the formula.

2. The compound according to claim 1,
wherein the compound contains 30 or fewer carbon atoms in total.

3. The compound according to claim 1,
wherein L is a single bond.

4. The compound according to claim 1,
wherein $R^2$ and $R^4$ are each H or a C1-C4 linear or branched alkyl group.

5. The compound according to claim 1,
wherein $R^3$ is a C1-C4 alkylene group free from a substituent.

6. The compound according to claim 1,
wherein X in the formula is $NR^5_4$.

7. The compound according to claim 1,
wherein the compound is an aqueous dispersant.

8. The compound according to claim 1, wherein the compound contains 10 to 30 carbon atoms in total.

9. The compound according to claim 1, wherein the compound contains 10 to 20 carbon atoms in total.

10. The compound according to claim 1, wherein A is —COOX and X is $NR^5_4$.

* * * * *